(12) United States Patent
Murthy Aravalli A V V L N et al.

(10) Patent No.: US 11,896,473 B2
(45) Date of Patent: Feb. 13, 2024

(54) SURGICAL MESH DEPLOYMENT DEVICE

(71) Applicant: Covidien LP, Mansfield, MA (US)

(72) Inventors: Srinivasa Murthy Aravalli A V V L N, Hyderabad (IN); Ravi Sekhar Gutti, Hyderabad (IN); Rajanikanth Mandula, Hyderabad (IN); Jitendra Bhargava Srinivas, Hyderabad (IN); Raja Kamaraj, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 256 days.

(21) Appl. No.: 17/332,013

(22) Filed: May 27, 2021

(65) Prior Publication Data

US 2022/0008185 A1     Jan. 13, 2022

Related U.S. Application Data

(60) Provisional application No. 63/050,967, filed on Jul. 13, 2020.

(51) Int. Cl.
*A61F 2/00* (2006.01)

(52) U.S. Cl.
CPC .... *A61F 2/0063* (2013.01); *A61F 2002/0072* (2013.01)

(58) Field of Classification Search
CPC ........................ A61F 2/0063; A61F 2002/0072
See application file for complete search history.

(56) References Cited

U.S. PATENT DOCUMENTS

| | | | |
|---|---|---|---|
| 5,122,155 A | | 6/1992 | Eberbach |
| 5,258,000 A | | 11/1993 | Gianturco |
| 5,263,969 A | | 11/1993 | Phillips |
| 5,304,187 A | | 4/1994 | Green et al. |
| 5,333,624 A | | 8/1994 | Tovey |
| 5,366,460 A | | 11/1994 | Eberbach |
| 5,370,650 A | | 12/1994 | Tovey et al. |
| 5,383,477 A | | 1/1995 | DeMatteis |
| 5,397,331 A | * | 3/1995 | Himpens .............. A61B 17/064 606/232 |
| 5,405,360 A | | 4/1995 | Tovey |
| 5,464,403 A | | 11/1995 | Kieturakis et al. |
| 5,713,948 A | | 2/1998 | Uflacker |
| 6,478,803 B1 | | 11/2002 | Kapec et al. |
| 6,575,988 B2 | | 6/2003 | Rousseau |
| 6,582,451 B1 | | 6/2003 | Marucci et al. |

(Continued)

FOREIGN PATENT DOCUMENTS

| | | |
|---|---|---|
| EP | 0706778 A1 | 4/1996 |
| FR | 2789888 A1 | 8/2000 |

(Continued)

*Primary Examiner* — Thaddeus B Cox
*Assistant Examiner* — Marc D. Honrath
(74) *Attorney, Agent, or Firm* — Carter, DeLuca & Farrell, LLP (57) ABSTRACT

A mesh deployment device is configured to place a surgical mesh on tissue retro muscularly. In particular, the mesh deployment device includes an arm assembly that is transitionable between a retracted configuration, in which, stationary and covering arms are in superposed relation such that the surgical mesh is supported by the supporting arm therebetween, and a deployed configuration, in which, the stationary, covering, and supporting arms are circumferentially spaced apart to support the surgical mesh thereon.

20 Claims, 4 Drawing Sheets

(56) References Cited

U.S. PATENT DOCUMENTS

| | | |
|---|---|---|
| 6,730,119 B1 | 5/2004 | Smalling |
| 7,591,813 B2 | 9/2009 | Levine et al. |
| 10,028,814 B2 | 7/2018 | Levin et al. |
| 2003/0135257 A1 | 7/2003 | Taheri |
| 2004/0073257 A1* | 4/2004 | Spitz .................... A61B 17/068 |
| | | 606/220 |
| 2004/0087980 A1 | 5/2004 | Ford et al. |
| 2004/0117032 A1 | 6/2004 | Roth |
| 2005/0131520 A1 | 6/2005 | Zilla |
| 2006/0189918 A1* | 8/2006 | Barker ............... A61B 17/0057 |
| | | 604/15 |
| 2007/0185506 A1* | 8/2007 | Jackson ................ A61F 2/0063 |
| | | 606/151 |
| 2007/0203507 A1 | 8/2007 | McLaughlin et al. |
| 2008/0188874 A1 | 8/2008 | Henderson |
| 2008/0195121 A1 | 8/2008 | Elder et al. |
| 2009/0248092 A1 | 10/2009 | Belles et al. |
| 2010/0234938 A1 | 9/2010 | Taheri |
| 2010/0312357 A1* | 12/2010 | Levin .................... A61B 17/064 |
| | | 623/23.72 |
| 2011/0230947 A1 | 9/2011 | Hartley |
| 2018/0256139 A1* | 9/2018 | Miller ....................... A61F 6/22 |

FOREIGN PATENT DOCUMENTS

| | | |
|---|---|---|
| WO | 2004080348 A1 | 9/2004 |
| WO | 2008045635 A2 | 4/2008 |
| WO | 2009104182 A2 | 8/2009 |
| WO | 2010046893 A1 | 4/2010 |

* cited by examiner

SURGICAL MESH DEPLOYMENT DEVICE

CROSS-REFERENCE TO RELATED APPLICATIONS

This application claims the benefit of and priority to U.S. Provisional Patent Application No. 63/050,967, filed Jul. 13, 2020, the entire contents of which is incorporated by reference herein.

TECHNICAL FIELD

The disclosure relates to surgical devices, and, more particularly, to a device for the deployment of a surgical mesh inside of a patient.

BACKGROUND

Hernias are abnormal protrusions of an organ or other body structure through a defect or natural opening in a covering membrane, muscle or bone. During surgical hernia repair procedures, surgical mesh materials are placed over the defect in the abdominal wall and are often sutured within the surgical opening by conventional suturing techniques. Traditionally, hernia repairs involved major invasive surgical procedures which often caused excessive trauma to the patient and necessitated long postoperative recuperative periods.

Recently, the use of laparoscopic and endoscopic surgical procedures has been relatively popular. In laparoscopic procedures, surgery is performed in the interior of the abdomen through narrow endoscopic tubes inserted through small entrance wounds in the skin.

SUMMARY

As used herein, the term "distal" refers to the portion that is being described which is further from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

In accordance with the disclosure, a mesh deployment device includes a body portion defining a lumen therethrough, a rotating knob rotatably supported on the body portion, an arm assembly operatively coupled with the rotating knob, and a surgical mesh secured to the arm assembly. The arm assembly includes a stationary arm coupled to the body portion, a covering arm coupled to the rotating knob for concomitant rotation therewith, and a supporting arm rotatably coupled with the covering arm. The arm assembly is transitionable between a retracted configuration, in which, the stationary and covering arms are in registration with each other such that the surgical mesh is folded between the stationary and covering arms by the supporting arm, and a deployed configuration, in which, the stationary and covering arms are circumferentially arranged to spread the surgical mesh.

In an aspect of the disclosure, the stationary arm may be non-rotatably fixed to the body portion.

In another aspect of the disclosure, the stationary arm may be distal of the covering arm.

In yet another aspect of the disclosure, the surgical mesh may define a slit.

In yet another aspect of the disclosure, the surgical mesh may have opposing first and second edges defining the slit. The opposing first and second edges may be secured with the respective stationary and covering arms.

In another aspect of the disclosure, the mesh deployment device may further include a string securing the surgical mesh to the arm assembly.

In yet another aspect of the disclosure, the body portion may define a lateral opening in communication with the lumen of the body portion. The string may extend from the arm assembly to the opening of the body portion through the lumen.

In yet another aspect of the disclosure, the stationary arm may include a first base, a first guide wall extending proximally from the first base, and a core extending proximally from the first base and connected to the body portion.

In still yet another aspect of the disclosure, the stationary arm may further include stoppers extending radially outward from the core.

In still yet another aspect of the disclosure, the covering arm may have a second base and a second guide wall extending distally from the second base and defining a first cutout.

In an aspect of the disclosure, the first and second guide walls may be on opposing sides of the arm assembly in the retracted configuration.

In another aspect of the disclosure, the first and second guide walls may be adjacent each other when the arm assembly is in the deployed configuration.

In yet another aspect of the disclosure, a first stopper of the core may be configured to engage the first cutout of the covering arm to limit amount of rotation of the covering arm.

In still yet another aspect of the disclosure, the supporting arm may include an engaging portion rotatably supported about the core of the stationary arm.

In still yet another aspect of the disclosure, the engaging portion of the supporting arm may define a second cutout configured to engage a second stopper of the core such that the second stopper limits amount of rotation of the supporting arm.

In an aspect of the disclosure, the stationary arm and the covering arm may define bores to receive a string therethrough.

In another aspect of the disclosure, a mesh deployment device includes a body portion, a rotating knob rotatably supported on the body portion, a surgical mesh, an arm assembly releasably securing the surgical mesh thereon. The arm assembly is operatively coupled to the rotating knob such that the arm assembly is rotatable about the body portion. The arm assembly includes a stationary arm coupled to the body portion, a covering arm coupled to the rotating knob for concomitant rotation therewith, and a supporting arm rotatably coupled with the covering arm. The arm assembly is transitionable between a retracted configuration, in which, the stationary and covering arms are in superposed relation such that the surgical mesh is supported by the supporting arm therebetween, and a deployed configuration, in which, the stationary, covering, and supporting arms are circumferentially spaced apart to support the surgical mesh thereon.

In an aspect of the disclosure, the arm assembly may be orthogonal to the body portion.

In another aspect of the disclosure, the stationary, covering, and supporting arms may be configured to rotate about the body portion by different amount.

In yet another aspect of the disclosure, the covering arm and the stationary arm may have respective atraumatic tips configured to dissect layers of tissue.

In still yet another aspect of the disclosure, the surgical mesh may have an arcuate profile defining a slit.

In yet another aspect of the disclosure, a mesh deployment device includes a rotating knob, an arm assembly operatively coupled with the rotating knob, and a surgical mesh secured to the arm assembly. The arm assembly includes a covering arm coupled to the rotating knob for concomitant rotation therewith and a supporting arm rotatably coupled with the covering arm. The arm assembly is transitionable between a retracted configuration, in which, the covering arm and the supporting arms are in registration with each other such that the surgical mesh is folded between the covering arm and the supporting arm, and a deployed configuration, in which, the covering arm and the supporting arm are spaced apart to spread the surgical mesh.

In an aspect, the covering arm and the supporting arm may be rotatable about a common axis.

BRIEF DESCRIPTION OF DRAWINGS

The above and other aspects and features of the disclosure will become more apparent in view of the following detailed description when taken in conjunction with the accompanying drawings wherein like reference numerals identify similar or identical elements.

DETAILED DESCRIPTION

Figure 1:
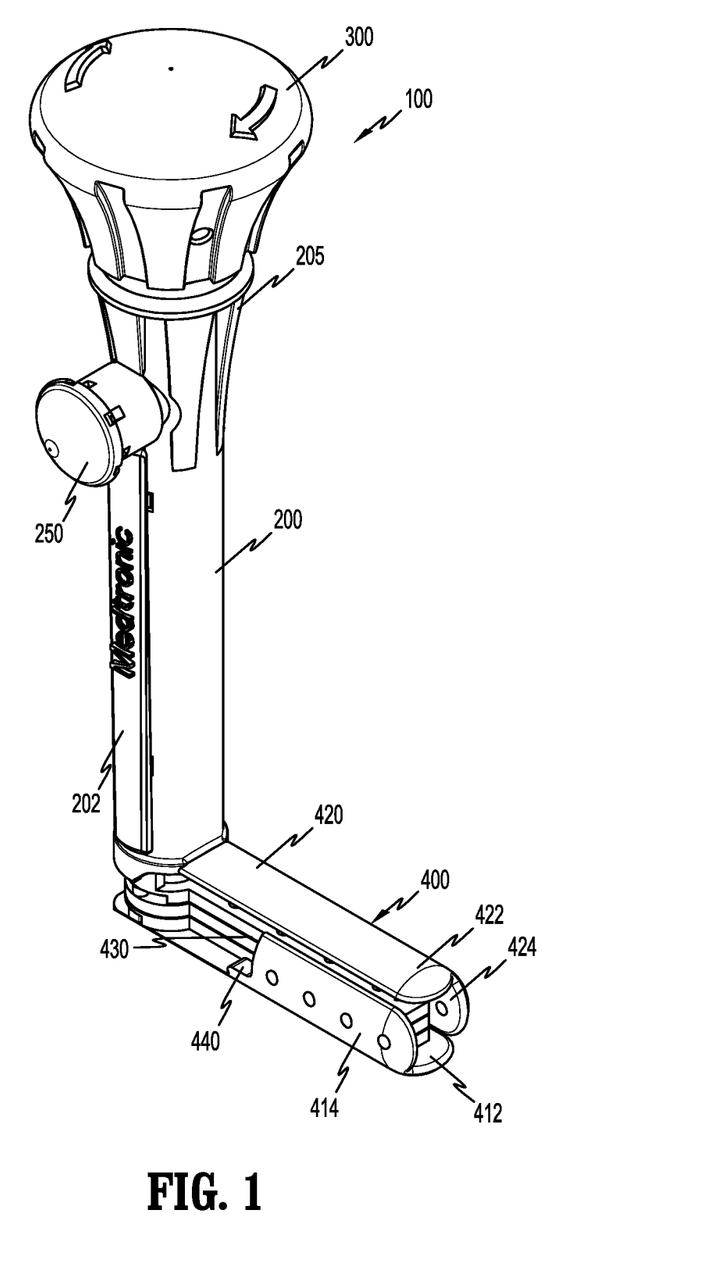
FIG. 1 is a perspective view of a mesh deployment device in accordance with the disclosure.

FIG. 1 illustrates an exemplary a mesh deployment device generally shown as 100 configured to place a surgical mesh 700 (FIG. 3) on tissue retro muscularly in order to avoid, e.g., parastomal hernia, in ostomy patients. Parastomal hernia is a type of incisional hernia occurring in abdominal integuments in the vicinity of a stoma, e.g., a condition wherein abdominal contents, typically the bowel or greater omentum, protrude through abdominal integuments surrounded by the hernia sac at the location of the formed stoma. Deploying a mesh below the peritoneum layer as a reinforcing structure may involve relatively complex maneuvers. However, use of the mesh deployment device 100 enables a clinician to deploy the surgical mesh 700 retro muscularly without requiring additional skill or training. In addition, placement of the surgical mesh 700 retro muscularly instead of below peritoneum layer eliminates the need for any collagen coating. The mesh deployment device 100 may be configured to be inserted through an incision in the range of about 12 mm and 15 mm.

The mesh deployment device 100 includes a body portion 200, a rotating knob 300, and an arm assembly 400. For example, the arm assembly 400 may be substantially orthogonal to the body portion 200. The mesh deployment device 100 is transitionable between a retracted configuration (FIG. 1), in which, the arm assembly 400 is configured to facilitate insertion of the surgical mesh 700 through an opening or an incision in tissue, and a deployed configuration (FIG. 3), in which, the arm assembly 400 is configured to spread the surgical mesh 700 over a desired location on tissue. The body portion 200 has a tubular configuration defining a lumen therethrough. The body portion 200 further defines an opening 210 (FIG. 4) on a lateral wall 202 of the body portion 200. The opening 210 is in communication with the lumen of the body portion 200. In particular, the body portion 200 further includes a cap 250 configured to be detachably disposed in the opening 210, and connected to a string 230 (FIG. 4), as will be discussed below.

The rotating knob 300 is operatively coupled with the arm assembly 400 to transition the arm assembly 400 between the retracted and deployed configurations. In particular, the rotating knob 300 is rotatably supported on a proximal end portion 205 of the body portion 200. The rotating knob 300 may be coupled to the arm assembly 400 by, e.g., a cable or a rod, extending through the lumen of the body portion 200 for concomitant rotation therewith.

Figure 2:
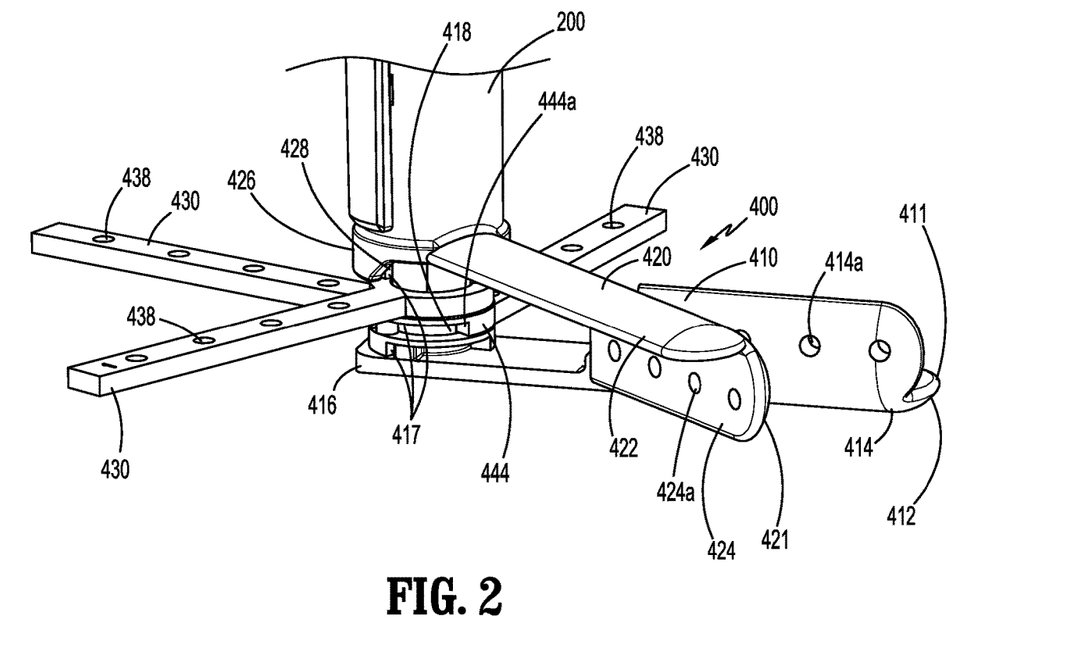
FIG. 2 is a partial perspective view of the mesh deployment device of FIG. 1, illustrating an arm assembly thereof.

FIG. 2 illustrates the arm assembly 400 in the deployed configuration without the surgical mesh 700. The arm assembly 400 includes a stationary arm 410 fixed to the body portion 200 to inhibit rotation relative to the body portion 200. The stationary arm 410 includes a base 412, a guide wall 414 extending proximally from one of the opposing sides of the base 412, and an engaging portion 416 in registration with the body portion 200. The engaging portion 416 includes a core 418 extending proximally from the base 412 and a plurality of stoppers 417 (only three stoppers shown in FIG. 2) extending radially outward from the core 418, as will be discussed below. The core 418 is coupled to the body portion 200.

In addition, the arm assembly 400 further includes a covering arm 420 and a plurality of supporting arms 430 rotatably coupled to the body portion 200. As best shown in FIG. 2, the covering arm 420 and the supporting arms 430 are rotatable about the core 418 of the stationary arm 410. In particular, the covering arm 420 is coupled to the rotating knob 300 for concomitant rotation therewith. For example, when the rotating knob 300 is rotated in the direction of an arrow "C" (FIG. 3), the covering arm 420 rotates in the direction of the arrow "C." The covering arm 420 is proximal of the supporting arms 430 such that the supporting arms 420 are interposed between the stationary arm 410 and the covering arm 420 in a superposed relation when the arm assembly 400 is in the retracted configuration. Under such a configuration, when the arm assembly 400 is in the retracted configuration, the guide walls 412, 424 of the respective stationary arm 410 and the covering arm 420 are on opposing sides of the arm assembly 400 to enable rotation of the covering arm 420 and the plurality of supporting arms 430 about the body portion 200. The guide walls 414, 424 of the stationary arm 410 and the covering arm 420 may define a width therebetween no greater than about 12 mm. The bases 412, 422 of the stationary arm 410 and the covering arm 420 may define a width therebetween no greater than about 12 mm. It is contemplated that the stationary arm 410 and the covering arm 420 may have respective blunt tips 411, 421 (FIG. 2) configured to separate layers of tissue. The blunt tips 411, 421 may also reduce trauma to tissue during contact with tissue.

Figure 3:
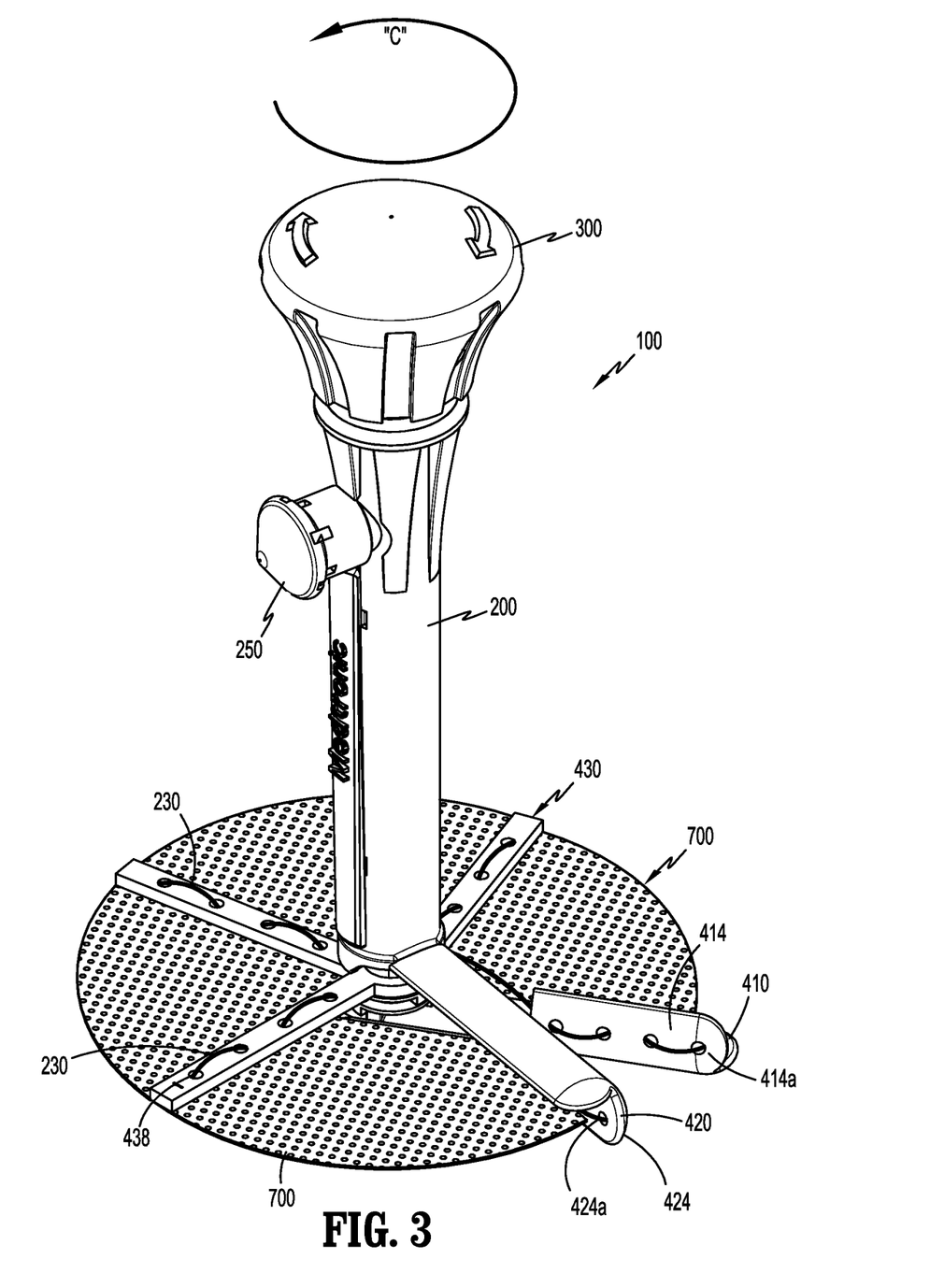
FIG. 3 is a perspective view of the mesh deployment device of FIG. 1, illustrating the arm assembly in a deployed configuration.

In particular, the covering arm 420 includes a base 422, a guide wall 424 extending distally from one of the opposing sides of the base 422, and an engaging portion 426 concentrically arranged with the body portion 200. In particular, the engaging portion 426 defines a circumferential cutout 428 configured to engage a proximal-most stopper 417 of the core 418 of the stationary arm 410. The proximal-most stopper 417 is positioned on the core 418 of the stationary arm 410 to enable rotation of the covering arm 420 by a pre-determined amount. For example, the stopper 417 may be placed to enable rotation of the covering arm 420 such that the guide wall 424 of the covering arm 420 is adjacent the guide wall 414 of the stationary arm 410 when the arm assembly 400 is in the deployed configuration, as shown in FIG. 3. Similarly, the other stoppers 417 are also circumferentially arranged to limit amount of rotation of the respective supporting arms 430. In particular, the stoppers 417 are circumferentially spaced apart to inhibit overlapping of the covering and supporting arms 420, 430 when the arm assembly 400 is in the deployed configuration. Under such a configuration, the arm assembly 400 may uniformly support the surgical mesh 700 when the surgical mesh 700 is deployed.

FIG. 2 further illustrates the supporting arms 430 including respective engaging portions 444 aligned with the body portion 200. Each engaging portion 444 defines a circumferential cutout 444a configured to engage a respective stopper 417 to limit amount of rotation of the supporting arm 430. The stoppers 417 are circumferentially arranged on the core 418 to enable the covering arm 420 and the supporting arms 430 to rotate by different amounts to provide uniform support of the surgical mesh on the arm assembly 400.

FIG. 3 illustrates the mesh deployment device 100 in the deployed configuration. In particular, the surgical mesh 700 is secured to the arm assembly 400 by a string or suture 230. However, it is also envisioned that the surgical mesh 700 may be secured to the arm assembly 400 by, e.g., sutures, clips, glue, staples, and/or locks. The guide walls 414, 424 of the respective stationary arm 410 and the covering arm 420 define a plurality of bores 414a, 424a to receive the string 230 therethrough. Furthermore, each supporting arm 430 defines a plurality of bores 438 configured to receive the string 230 therethrough. Under such a configuration, the string 230 may be utilized to secure the surgical mesh 700 to the arm assembly 400. Ends of the string 230 may be connected to the cap 250 such that after the surgical mesh 700 is secured to tissue by, e.g., tack or suture (not shown), the string 230 connecting the surgical mesh 700 to the arm assembly 400 may be cut by the clinician and the string 230 may be removed from the surgical site by pulling the cap 250 away from the body portion 200, as shown in FIG. 4.

The rotating knob 300 may be rotatably coupled to the covering arm 420 for concomitant rotation therewith. The covering arm 420 and the supporting arms 430 may cammingly engage each other. The covering arm 420 may be configured to cause rotation of an adjacent supporting arm 430 distal of the covering arm 420 during rotation of the covering arm 420. Rotation of the proximal-most supporting arm 430 may cause rotation of an adjacent supporting arm 430 distal of the proximal-most supporting arm 430 by a predetermined amount. Rotation of the middle supporting arm 430 may cause rotation of the distal-most supporting arm 430 in a similar manner. However, the stoppers 417 limit the amount of rotation of the covering arm 420 and the supporting arms 430. Alternatively, the covering arm 420 and the supporting arms 430 may be independently coupled to the rotating knob 300 for independent rotation thereof by a respective predetermined amount of rotation.

Figure 4:
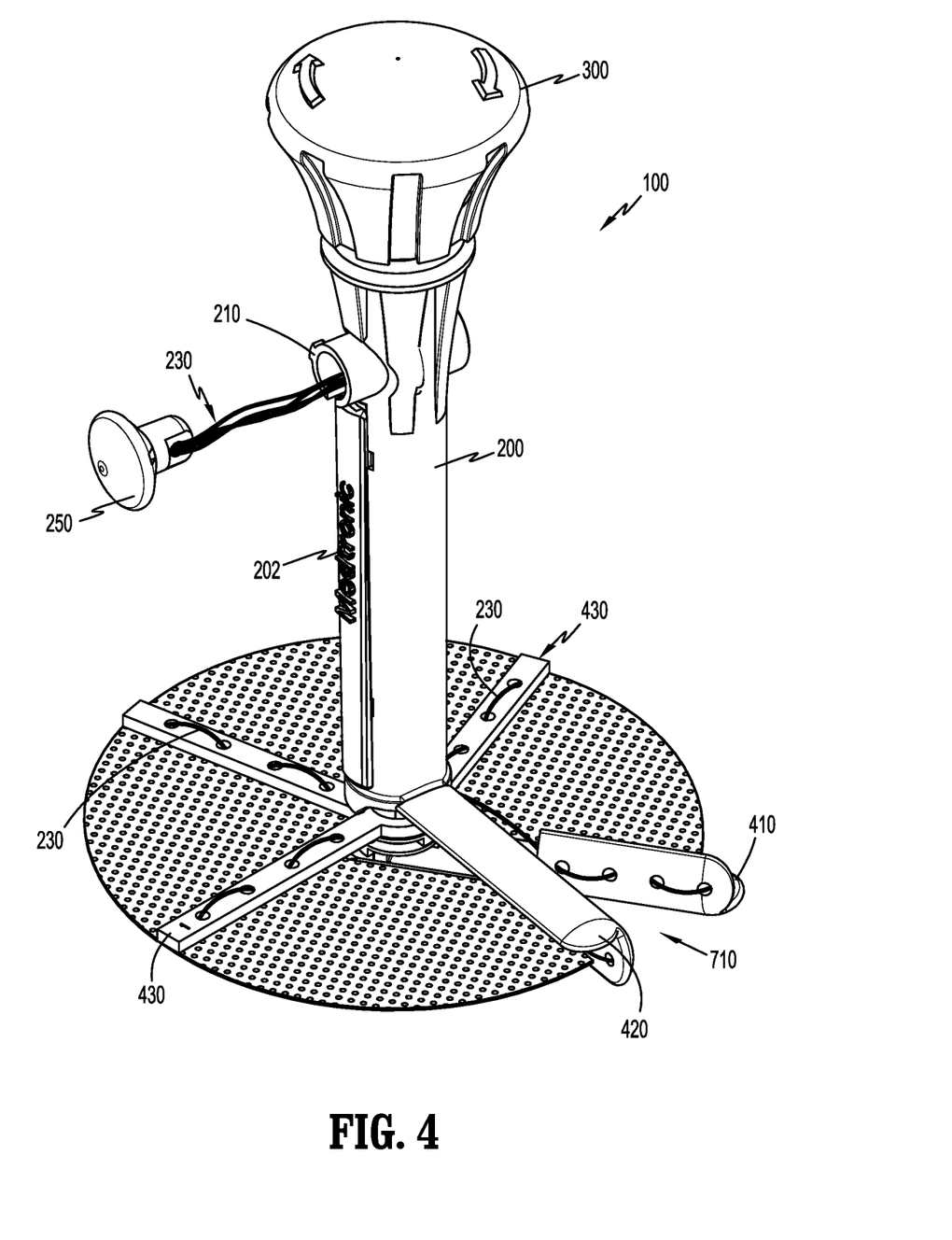
FIG. 4 is a perspective view of the mesh deployment device of FIG. 1, illustrating a string pulled out of an opening of a body portion of the mesh deployment device.

FIG. 4 illustrates the surgical mesh 700 in the deployed configuration. The surgical mesh 700 includes an arcuate shape defining a slit 710 such that portions of the surgical mesh 700 defining the slit 710 are securable to the respective stationary arm 410 and the covering arm 420. In the deployed configuration, the supporting arms 430 may be arranged to provide substantially uniform support to the surgical mesh 700. The surgical mesh 700 may be made of a bio-compatible material. It is also envisioned that the surgical mesh 700 may have a solid inner configuration and a mesh outer configuration. Alternately, the surgical mesh 700 may have a mesh inner configuration which is tightly woven and a mesh outer configuration which is loosely woven. One example of the surgical mesh 700 may include a polypropylene material marketed by C. R. Bard, under the trademark MARLEX. Another example of the surgical mesh 700 may be a tri-fluoroethylene material marketed by W. L. Gore & Associates, Newark, Delaware, under the trademark GORE-TEX. As discussed hereinabove, the mesh deployment device 100 eliminates the need for collagen coating on the surgical mesh 700.

In use, the arm assembly 400 is transitioned to the deployed configuration (FIG. 2). The surgical mesh 700 is secured to the arm assembly 400 using the string 230 (FIG. 1) coupled to the cap 250. The arm assembly 400 is then transitioned to the retracted position (FIG. 1) such that the surgical mesh 700 is received between the stationary arm 410 and the covering arm 420, whereby the surgical mesh 700 is folded or wrapped between the supporting arms 430. Thereafter, the surgical site is prepared by the clinician. In particular, the clinician may dissect layers of tissue using a balloon dissector known in the art or using fingers to provide space for insertion of the arm assembly 400 retro muscularly. Thereafter the clinician inserts the arm assembly 400 through an incision. Once the arm assembly 400 is placed adjacent the surgical site, the rotating knob 300 is rotated to transition the arm assembly 400 to the deployed configuration. Once the surgical mesh 700 is placed over the surgical site, the surgical mesh 700 may be attached to tissue using, e.g., tacks or stitch, as known in the art. Thereafter, the string 230 may be cut in order to detach the surgical mesh 700 from the arm assembly 400. At this time, the clinician may pull on the string 230 by pulling the cap 250 out of the opening 210 on the body portion 200. The mesh deployment device 100 may be removed from the patient by transitioning the arm assembly 400 back to the retracted configuration to fit through the incision. The mesh deployment device 100 reduces risk for complications and trauma to patient. Further, the mesh deployment device 100 has simple mechanism and assembly, which, in turn, reduces costs of maintenance and manufacture.

It will be understood that various modifications may be made to the mesh deployment device 100. Therefore, the above description should not be construed as limiting, but merely as exemplifications. Those skilled in the art will envision other modifications within the scope and spirit of the claims appended thereto. For example, the mesh deployment device 100 may be adapted for use with robotic surgery systems.

While aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. A mesh deployment device comprising:
a body portion defining a lumen;
a rotating knob rotatably supported on the body portion;
an arm assembly operatively coupled with the rotating knob, the arm assembly including:
a stationary arm coupled to the body portion;
a covering arm coupled to the rotating knob for concomitant rotation with the rotating knob; and
a supporting arm rotatably coupled with the covering arm; and
a surgical mesh secured to the arm assembly,
wherein the arm assembly is transitionable between a retracted configuration, in which, the stationary and covering arms are in registration with each other such that the surgical mesh is folded between the stationary arm and the covering arm by the supporting arm, and a deployed configuration, in which, the stationary arm and the covering arm are circumferentially arranged to spread the surgical mesh.

2. The mesh deployment device according to claim 1, wherein the stationary arm is non-rotatably fixed to the body portion.

3. The mesh deployment device according to claim 2, wherein the stationary arm is distal of the covering arm.

4. The mesh deployment device according to claim 1, wherein the surgical mesh defines a slit.

5. The mesh deployment device according to claim 4, wherein the surgical mesh has a first edge and a second edge, and wherein the slit is defined in the first edge and the second edge, the first edge and second edge being secured with the respective stationary arm and covering arm.

6. The mesh deployment device according to claim 1, further comprising a string securing the surgical mesh to the arm assembly.

7. The mesh deployment device according to claim 6, wherein the body portion defines a lateral opening in communication with the lumen of the body portion, the string extending from the arm assembly to the opening of the body portion through the lumen.

8. The mesh deployment device according to claim 1, wherein the stationary arm includes a first base, a first guide wall extending proximally from the first base, and a core extending proximally from the first base and connected to the body portion.

9. The mesh deployment device according to claim 8, wherein the stationary arm further includes stoppers extending radially outward from the core.

10. The mesh deployment device according to claim 9, wherein the covering arm has:
a second base; and
a second guide wall extending distally from the second base and defining a first cutout.

11. The mesh deployment device according to claim 10, wherein the first guide wall and the second guide wall are on opposing sides of the arm assembly in the retracted configuration.

12. The mesh deployment device according to claim 10, wherein the first guide wall and the second guide wall are adjacent each other when the arm assembly is in the deployed configuration.

13. The mesh deployment device according to claim 10, wherein a first stopper of the core is configured to engage the first cutout of the covering arm to limit an amount of rotation of the covering arm.

14. The mesh deployment device according to claim 10, wherein the supporting arm includes an engaging portion rotatably supported about the core of the stationary arm.

15. The mesh deployment device according to claim 14, wherein the engaging portion of the supporting arm defines a second cutout configured to engage a second stopper of the core such that the second stopper limits an amount of rotation of the supporting arm.

16. The mesh deployment device according to claim 14, wherein the stationary arm and the covering arm define bores to receive a string therethrough.

17. A mesh deployment device comprising:
a body portion;
a rotating knob rotatably supported on the body portion;
a surgical mesh; and
an arm assembly releasably securing the surgical mesh, the arm assembly operatively coupled to the rotating knob such that the arm assembly is rotatable about the body portion, the arm assembly including:
a stationary arm coupled to the body portion;
a covering arm coupled to the rotating knob for concomitant rotation with the rotating knob; and
a supporting arm rotatably coupled with the covering arm,
wherein the arm assembly is transitionable between a retracted configuration, in which, the stationary arm and the covering arm are in superposed relation such that the surgical mesh is supported by the supporting arm, and a deployed configuration, in which, the stationary arm, the covering arm, and the supporting arm are circumferentially spaced apart to support the surgical mesh.

18. The mesh deployment device according to claim 17, wherein the arm assembly is orthogonal to the body portion.

19. A mesh deployment device comprising:
a stationary arm coupled to an elongate body portion, the stationary arm extending at an angle relative to a longitudinal axis of the elongate body portion;
a rotating knob rotatably supported in the elongate body portion for rotation about the longitudinal axis of the elongate body portion;
an arm assembly operatively coupled with the rotating knob, the arm assembly including:
a covering arm coupled to the rotating knob for concomitant rotation with the rotating knob and relative to the covering arm, the covering arm extending parallel to the stationary arm; and
a supporting arm rotatably coupled to the rotating knob for concomitant rotation with the rotating knob and relative to the covering arm, the supporting arm extending parallel to the stationary arm and between the stationary arm and the covering arm; and
a surgical mesh secured to the stationary arm and to each of the covering arm and the supporting arm of the arm assembly,
wherein the arm assembly is transitionable between a retracted configuration, in which, the stationary arm, the covering arm and the supporting arm are in registration with each other such that the surgical mesh is folded between the stationary arm, the covering arm and the supporting arm, and a deployed configuration, in which, the stationary arm, the covering arm and the supporting arm are spaced apart to spread the surgical mesh.

20. The mesh deployment device according to claim 19, wherein the covering arm and the supporting arm are rotatable about a common axis relative to the stationary arm.

\* \* \* \* \*